(12) United States Patent
Watanabe

(10) Patent No.: US 10,743,802 B2
(45) Date of Patent: Aug. 18, 2020

(54) PROBE

(71) Applicant: NIHON KOHDEN CORPORATION, Shinjuku-ku, Tokyo (JP)

(72) Inventor: Nobuyoshi Watanabe, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 102 days.

(21) Appl. No.: 15/543,058

(22) PCT Filed: Mar. 4, 2016

(86) PCT No.: PCT/JP2016/001211
§ 371 (c)(1),
(2) Date: Jul. 12, 2017

(87) PCT Pub. No.: WO2016/143319
PCT Pub. Date: Sep. 15, 2016

(65) Prior Publication Data
US 2018/0014757 A1 Jan. 18, 2018

(30) Foreign Application Priority Data
Mar. 10, 2015 (JP) .................. 2015-047235

(51) Int. Cl.
*A61B 5/1455* (2006.01)
*A61B 5/024* (2006.01)
(Continued)

(52) U.S. Cl.
CPC .......... *A61B 5/1455* (2013.01); *A61B 5/0059* (2013.01); *A61B 5/0082* (2013.01);
(Continued)

(58) Field of Classification Search
None
See application file for complete search history.

(56) References Cited

U.S. PATENT DOCUMENTS

| | | |
|---|---|---|
| 4,971,062 A | 11/1990 | Hasebe et al. |
| 5,065,749 A | 11/1991 | Hasebe et al. |

(Continued)

FOREIGN PATENT DOCUMENTS

| | | |
|---|---|---|
| CN | 201098123 Y | 8/2008 |
| EP | 0 790 800 A1 | 8/1997 |

(Continued)

OTHER PUBLICATIONS

Japanese Office action issued in Patent Application No. JP-2015-047235 dated Jun. 26, 2018.

(Continued)

*Primary Examiner* — Etsub D Berhanu
(74) *Attorney, Agent, or Firm* — Pearne & Gordon LLP

(57) ABSTRACT

A biological signal acquirer is attached to a subject and acquires a biological signal of the subject. A transmitter carried by the subject transmits the biological signal. A first communication port and a first camera are installed in a first location and connectable to a network. A second communication port and a second camera are installed in a second location and connectable to the network. A biological information acquiring device is connectable to the network and provided with a switcher. The switcher acquires, when communication establishment between the transmitter and the first communication port is detected, the biological signal through the first communication port as well as a first image taken by the first camera, and acquires, when communication establishment between the transmitter and the second communication port is detected, the biological signal through the second communication port as well as a second image taken by the second camera.

17 Claims, 3 Drawing Sheets

(51) Int. Cl.
*A61B 5/026* (2006.01)
*A61B 5/00* (2006.01)
*A61B 5/0245* (2006.01)

(52) U.S. Cl.
CPC .......... *A61B 5/0245* (2013.01); *A61B 5/0261* (2013.01); *A61B 5/02427* (2013.01); *A61B 5/02444* (2013.01); *A61B 5/6826* (2013.01); *A61B 5/6838* (2013.01); *A61B 2562/0242* (2013.01)

(56) References Cited

U.S. PATENT DOCUMENTS

| | | | | |
|---|---|---|---|---|
| 6,041,246 | A * | 3/2000 | Krivitski | A61B 5/14557 600/322 |
| 2001/0009265 | A1 | 7/2001 | Schulz et al. | |
| 2002/0026109 | A1 * | 2/2002 | Diab | A61B 5/02427 600/344 |
| 2003/0023171 | A1 * | 1/2003 | Sato | A61B 5/14552 600/476 |
| 2005/0002031 | A1 | 1/2005 | Kraemer et al. | |
| 2012/0197093 | A1 | 8/2012 | LeBoeuf et al. | |
| 2015/0018654 | A1 | 1/2015 | Mestha et al. | |

FOREIGN PATENT DOCUMENTS

| | | |
|---|---|---|
| EP | 1 880 665 A1 | 1/2008 |
| JP | H02-088041 A | 3/1990 |
| JP | H10-509352 A | 9/1998 |
| JP | 2003-507718 A | 2/2003 |
| WO | 96/13208 A1 | 5/1996 |
| WO | 01-13790 A1 | 3/2001 |

OTHER PUBLICATIONS

International Search Report issued in Patent Application No. PCT/JP2016/001211 dated May 30, 2016.
Written Opinion issued in Patent Application No. PCT/JP2016/001211 dated May 30, 2016.
Chinese Office action issued in Patent Application No. 201680015112.1 dated Sep. 4, 2019.

* cited by examiner

[Fig. 1A]
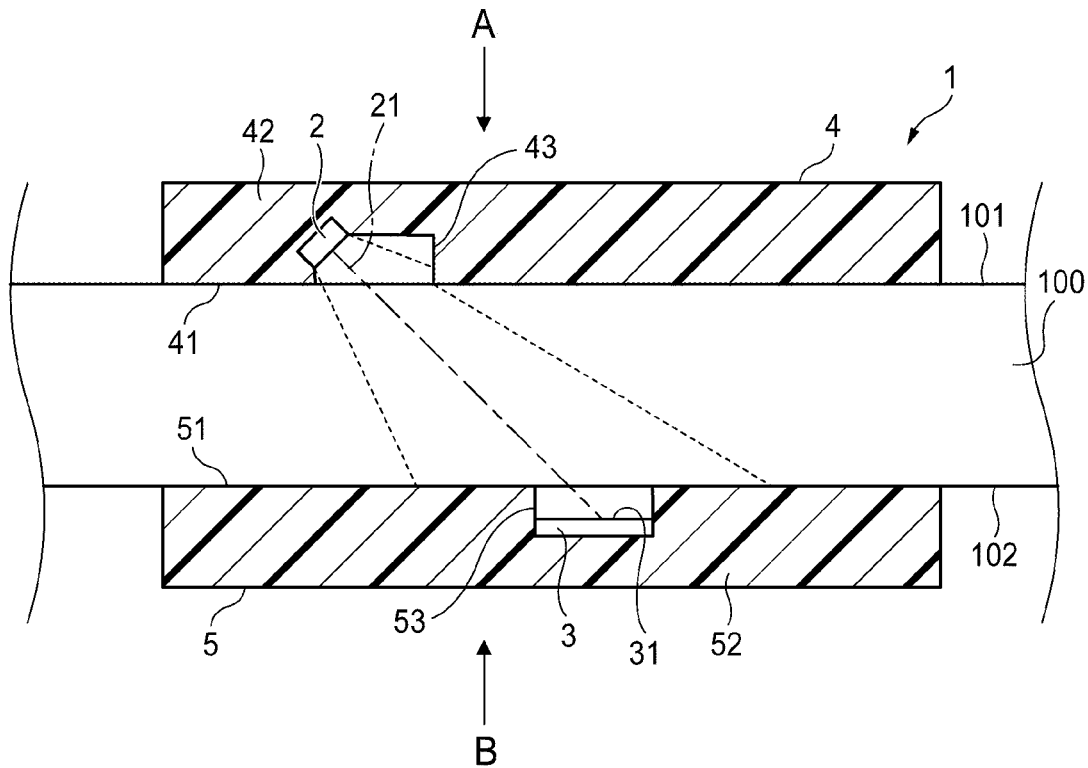
[Fig. 1B]
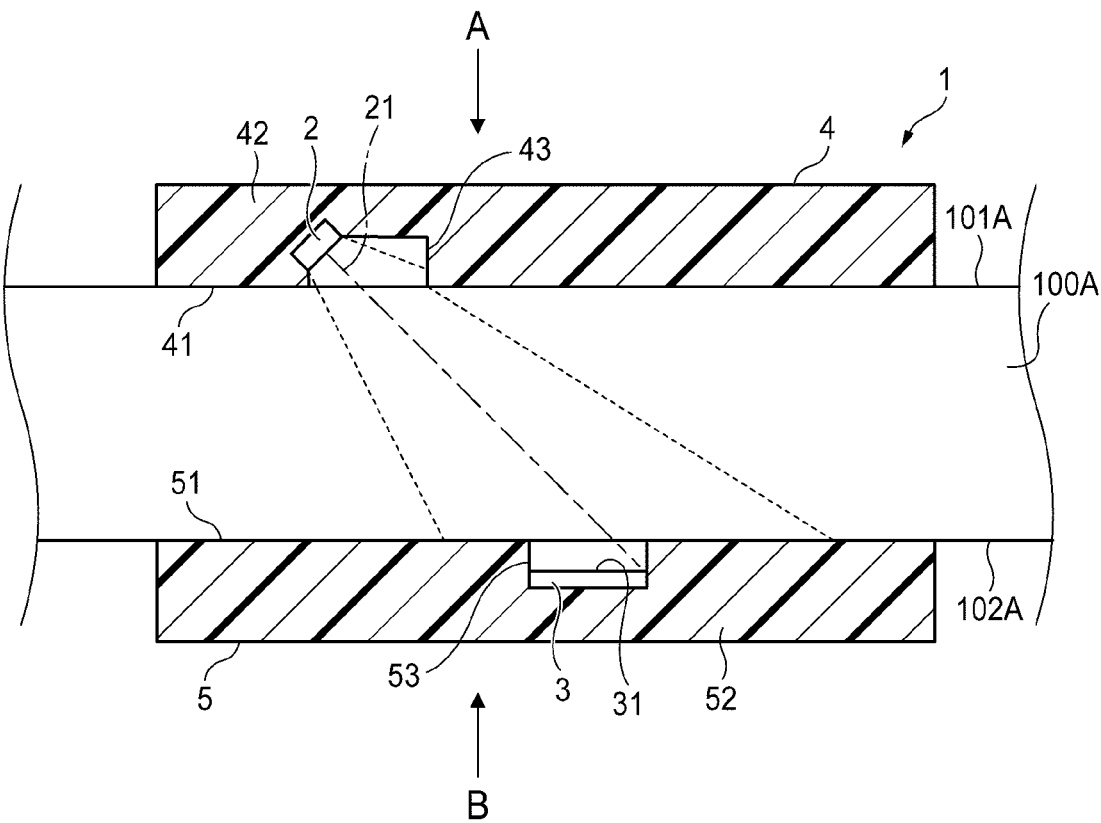

[Fig. 2A]
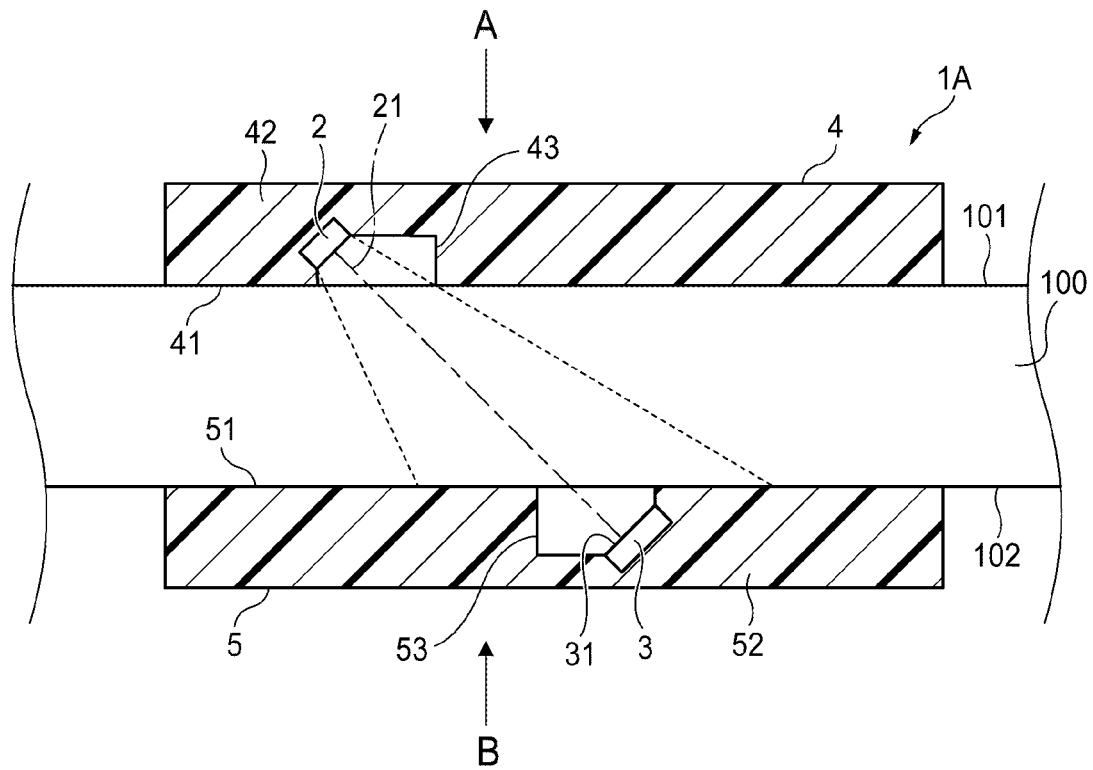
[Fig. 2B]
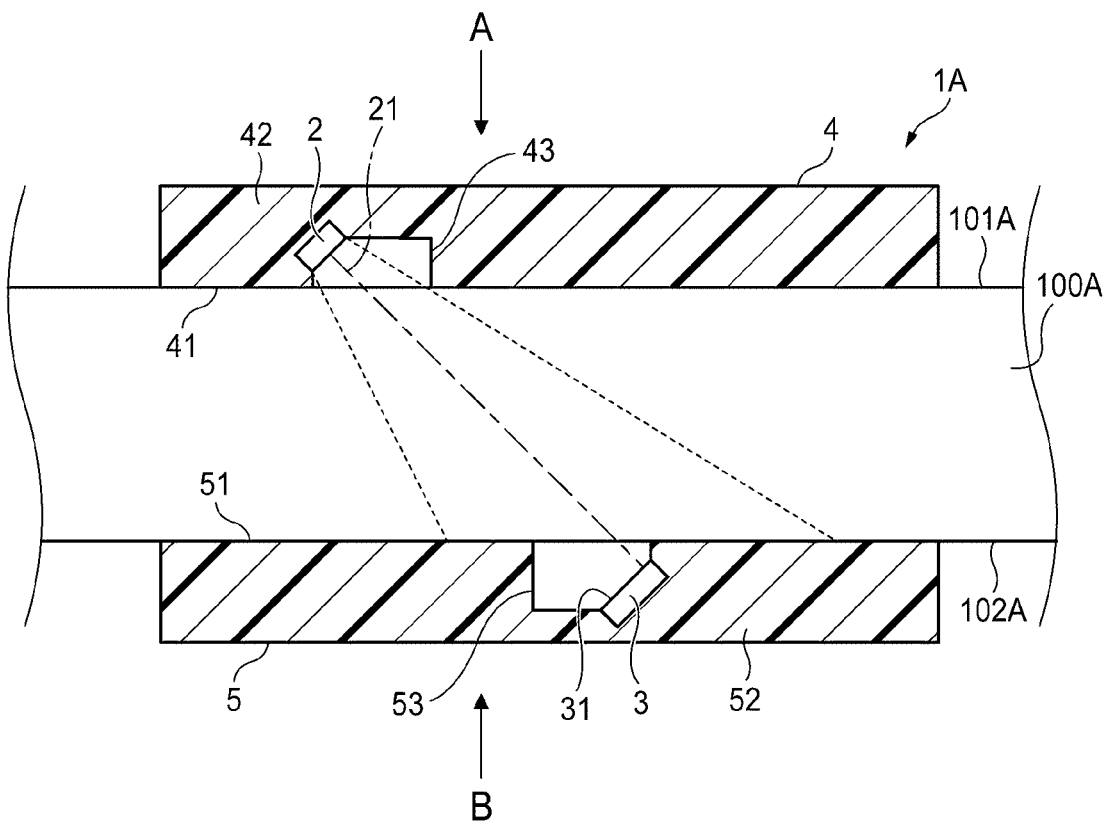

[Fig. 3A]
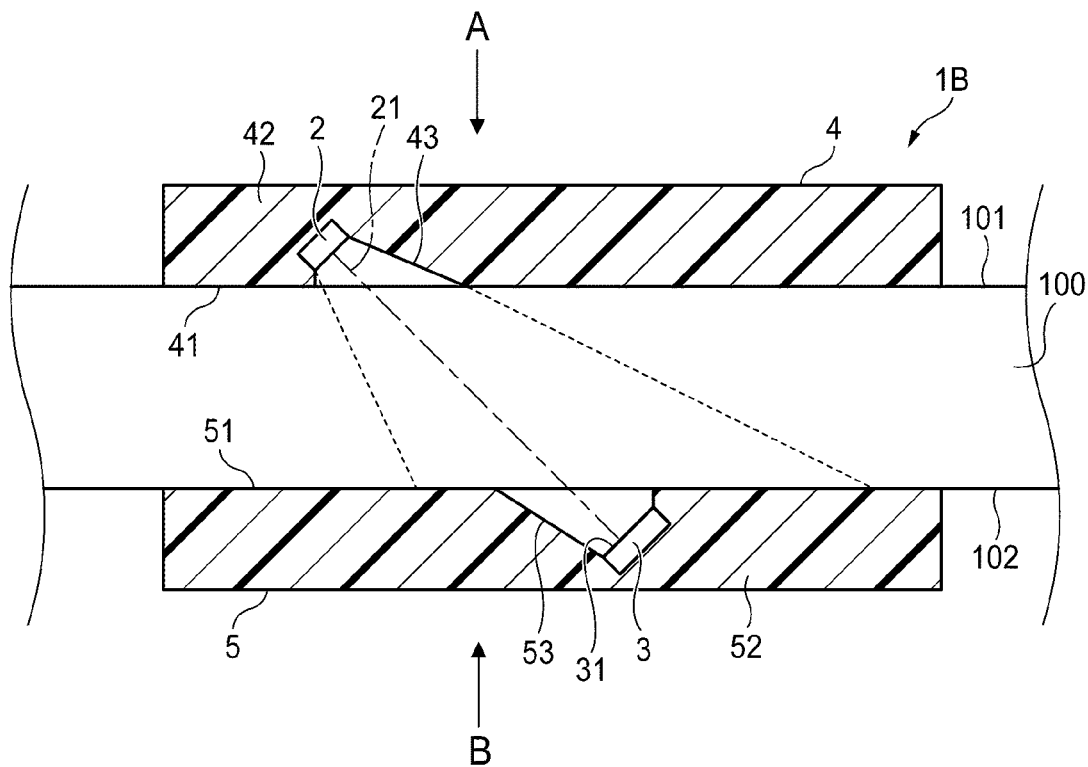
[Fig. 3B]
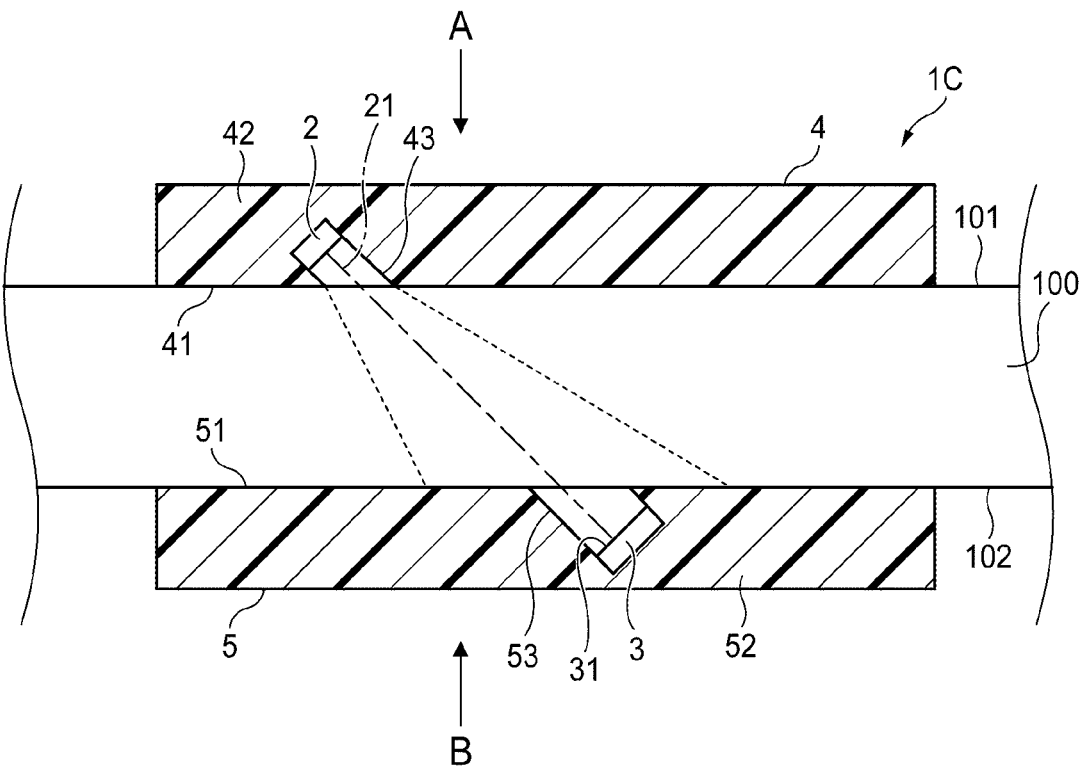

ial signal of the
PROBE

TECHNICAL FIELD

The present invention relates to a probe which is to be attached to the living tissue of a subject, and which is configured to be able to output a biological signal of the subject to an apparatus for acquiring the biological signal.

BACKGROUND ART

Patent Literature 1 discloses a probe which is to be attached to the fingertip of a subject. The probe includes a light-emitting element and a light-detecting element. The light-detecting element has a light-detecting surface configured to detect light that has been emitted from the light-emitting element, and that has been transmitted through the living tissue of the fingertip. The light-detecting element is configured to output a signal corresponding to the intensity of the light which has been detected by the light-detecting surface. The light emitted from the light-emitting element is determined to have a wavelength which is to be absorbed by a material in blood. The volume of blood in the fingertip is changed in accordance with the pulse, and therefore the intensity of the light which is detected by the light-detecting surface is changed as well. The signal output from the light-detecting element is used for calculating biological information of the subject, such as the pulse and the arterial oxygen saturation.

CITATION LIST

Patent Literature

PTL 1: Japanese Patent Publication No. H02-088041A

SUMMARY OF INVENTION

Technical Problem

There is a case where the above-described probe is attached to a part such as an earlobe or a skin of a neonatal infant a living tissue of which is thin. In a case where the living tissue is thin, there might be a case where biological signals are not accurately acquired.

The object of the invention is to accurately acquire biological signals irrespective of the thickness of the living tissue of the subject to which a probe is attached.

In order to achieve the above object, one aspect of the invention that can take is a probe comprising:

a light-emitting element having an optical axis;

a light-detecting element having a light-detecting surface configured to detect light emitted from the light-emitting element, and configured to output a signal in accordance with intensity of the light;

a first support having: a first attachment surface adapted to be attached to a first portion of a living tissue of a subject; a first supporting portion supporting the light-emitting element; and a first passage configured to allow the light emitted from the light-emitting element to pass through; and a second support having: a second attachment surface adapted to be attached to a second portion of the living tissue of the subject; a second supporting portion supporting the light-detecting element; and a second passage configured to allow the light having passed through the second portion to pass through, wherein the light-emitting element is supported by the first supporting portion such that the optical axis is inclined relative to a direction orthogonal to the first attachment surface;

wherein the light-detecting element is supported by the second supporting portion such that the optical axis is placed on the light-detecting surface under a condition that the first attachment surface is attached to the first portion of the living tissue and the second attachment surface is attached to the second portion of the living tissue; and wherein the second passage is located so as not to overlap with the first passage as seen from a direction orthogonal to the second attachment surface under the condition that the first attachment surface is attached to the first portion of the living tissue and the second attachment surface is attached to the second portion of the living tissue.

With the above configuration, it is possible to accurately acquire biological signals irrespective of the thickness of the living tissue of the subject to which the probe is attached.

BRIEF DESCRIPTION OF DRAWINGS

FIG. 1A illustrates a configuration of a probe according to a first embodiment,

FIG. 1B illustrates the configuration of the probe according to the first embodiment.

FIG. 2A illustrates a configuration of a probe according to a second embodiment.

FIG. 2B illustrates the configuration of the probe according to the second embodiment.

FIG. 3A illustrates a configuration of a first modified example of the probe of the second embodiment.

FIG. 3B illustrates a configuration of a second modified example of the probe of the second embodiment.

DESCRIPTION OF EMBODIMENTS

Exemplified embodiments will be described below in detail with reference to the accompanying drawings.

FIG. 1A schematically illustrates the configuration of a probe 1 according to a first embodiment. The probe 1 comprises a light-emitting element 2, a light-detecting element 3, a first support 4, and a second support 5. The probe 1 is adapted to be attached to a living tissue 100 of a subject. Fingertips, toe tips, earlobes can be exemplified as the living tissue 100.

The light-emitting element 2 is configured to emit light having a predetermined wavelength. The predetermined wavelength is determined as a wavelength which can be absorbed by a material in blood. The material is determined in accordance with the kind of the biological information to be calculated. In a case where the pulse or the arterial oxygen saturation is to be calculated, for example, oxyhemoglobin is selected as the material. In this case, a red light and an infrared light are selected as examples of the predetermined wavelength.

For example, the light-emitting element 2 is a semiconductor light emitting device configured to emit light having the predetermined wavelength. A light emitting diode (LED), a laser diode, and an organic EL device can be exemplified as the semiconductor light emitting device.

The light-emitting element 2 has an optical axis 21. In the specification, the optical axis 21 is defined as an axis extending in the direction in which the light emitted from the light-emitting element 2 has the highest intensity.

The light-detecting element 3 has a light-detecting surface 31 configured to detect light that has been transmitted through the living tissue 100. The light-detecting element 3 is configured to output an intensity signal in accordance with the intensity of the light which has been detected by the light-detecting surface 31. The intensity signal corresponds to the biological signal. The volume of the living tissue 100 to which the probe 1 is attached is changed in accordance with the pulse of the subject. Therefore, the intensity of the light which has been detected by the light-detecting surface 31 is changed. Thus, the intensity signal which is output from the light-detecting element 3 is changed as well.

The signal output from the light-detecting element 3 is transmitted to a biological signal acquiring apparatus through wired or wireless communication. The biological signal acquiring apparatus is configured to acquire desired biological information from changes of the intensity signal based on a predetermined algorithm. A pulse photometer and a bedside monitor can be exemplified as the biological signal acquiring apparatus.

For example, the light-detecting element 3 is an optical sensor having a sensitivity to the above-described predetermined wavelength. A photodiode, a phototransistor, and a photoresistor can be exemplified as the optical sensor.

The first support 4 has a first attachment surface 41. The first attachment surface 41 is adapted to be attached to a first portion 101 of the living tissue 100. A nail-side portion of a fingertip, a nail-side portion of a toe tip, and a front-side portion of an earlobe can be exemplified as the first portion 101.

The first support 4 has a first supporting portion 42. The first supporting portion 42 is supporting the light-emitting element 2.

The first support 4 has a first passage 43. The first passage 43 is configured to allow the light emitted from the light-emitting element 2 to pass through.

The second support 5 has a second attachment surface 51. The second attachment surface 51 is adapted to be attached to a second portion 102 of the living tissue 100. A pad-side portion of the fingertip, a pad-side portion of the toe tip, and a back-side portion of the earlobe can be exemplified as the second portion 102.

The second support 5 has a second supporting portion 52. The second supporting portion 52 is supporting the light-detecting element 3.

The second support 5 has a second passage 53. The second passage 53 is configured to allow the light emitted from the light-emitting element 2 to pass through.

The light-emitting element 2 is supported by the first supporting portion 42 so that the optical axis 21 is inclined with respect to the direction orthogonal to the first attachment surface 41 (the direction indicated by the arrow A in the figure).

The light-detecting element 3 is supported by the second supporting portion 52 so that the optical axis 21 is positioned on the light-detecting surface 31 under a condition that the first attachment surface 41 is attached to the first portion 101 of the living tissue 100 and that the second attachment surface 51 is attached to the second portion 102 of the living tissue 100.

Under the condition that the first attachment surface 41 is attached to the first portion 101 of the living tissue 100 and that the second attachment surface 51 is attached to the second portion 102 of the living tissue 100, the second passage 53 is located so as not to overlap with the first passage 43 as seen from the direction orthogonal to the second attachment surface 51 (the direction indicated by the arrow B in the figure).

FIG. 1B illustrates a case Where the probe 1 is attached to a living tissue 100A which is thicker than the living tissue 100 shown in FIG. 1A. The reference numeral 101A denotes a first portion of the living tissue 100A. The reference numeral 102A denotes a second portion of the living tissue 100A. Similarly to the above case, the optical axis 21 of the light-emitting element 2 is positioned on the light-detecting surface 31 of the light-detecting element 3. Moreover, the second passage 53 is located so as not to overlap with the first passage 43 as seen from the direction orthogonal to the second attachment surface 51 (the direction indicated by the arrow B in the figure).

The inventor investigated why the accuracy of a calculated biological information is lowered in the case where a probe is attached to a portion of thin living tissue, such as the earlobe or the skin of a neonatal infant. As a result, it was found that there are two causes.

A light-detecting element is configured to output an intensity signal having a potential corresponding to the light intensity which is detected by a light-detecting surface. However, the potential of the output signal has an upper limit which corresponds to the driving voltage of the element. When the input light intensity exceeds a certain value, therefore, the potential of the output signal is saturated to have a fixed value. In the case where the living tissue is thin, the transmitted light intensity is increased, and therefore this situation easily occurs. In this case, the intensity signal output from the light-detecting element no longer reflects the current state of the detection target. This is a first cause that the biological signal is not accurately acquired and the accuracy of the calculated biological information is lowered.

The larger the amount of blood located on the optical path length extending from the light-emitting element to a light-detecting element, the larger the volume change due to the pulse, and the more easily a significant change appears in the intensity signal. In the case where the living tissue is thin, however, the intensity of the detected light is high whereas the degree of a change appearing in the intensity signal is small. That is, the SN ratio of the intensity signal is reduced. This is a second cause that the biological signal is not accurately acquired and the accuracy of the calculated biological information is lowered.

In order to solve the problems, the inventor attempted to intentionally deviate the optical axis of the light-emitting element from the light-detecting surface of the light-detecting element. Namely, the light-emitting element and the light-detecting element are placed so that, under a condition that the probe is attached to the living tissue of the subject, the optical axis of the light-emitting element is not positioned on the light-detecting surface of the light-detecting element. In this case, scattered light which is mainly produced in the living tissue enters the light-detecting surface.

As a result, the intensity of light which is transmitted through the living tissue, and which then enters the light-detecting surface is lowered, and the reduction of the accuracy of biological information and due to saturation of the light-detecting element can be suppressed. In the case where the living tissue of the subject is relatively thick, however, the inventor faced a situation where the accuracy of calculated biological information is lowered. It can be considered that this is caused by a phenomenon the absolute value of the amount of the detected light is reduced by the intentional deviation of the optical axis of the light-emitting element from the light-detecting surface of the light-detecting element, so that the signal intensity is weakened.

As a result of thorough consideration, the inventor found that, in a case where the probe 1 simultaneously satisfies the following conditions, the biological signal can be accurately acquired irrespective of the thickness of the living tissue of the subject.

Condition 1: the second passage 53 is located so as not to overlap with the first passage 43 as seen from the direction B orthogonal to the second attachment surface 51, under the condition that the first attachment surface 41 is attached to the first portion 101 of the living tissue 100, and the second attachment surface 51 is attached to the second portion 102 of the living tissue 100.

Condition 2: the light-emitting element 2 is supported by the first supporting portion 42 so that the optical axis 21 is inclined with respect to the direction A orthogonal to the first attachment surface 41.

Condition 3: the light-detecting element 3 is supported by the second supporting portion 52 so that the optical axis 21 is positioned on the light-detecting surface 31 under the condition that the first attachment surface 41 is attached to the first portion 101 of the living tissue 100, and the second attachment surface 51 is attached to the second portion 102 of the living tissue 100.

Mainly due to Condition 1, it is possible to suppress the intensity of the light which is passed through the second passage 53, and which then enters the light-detecting surface 31 of the light-detecting element 3. Even in the case where the probe 1 is attached to the living tissue 100 that is relatively thin, therefore, the reduction of the accuracy of the acquisition of a biological signal and due to saturation of the light-detecting element 3 can be suppressed. Mainly due to Condition 2, the light emitted from the light-emitting element 2 obliquely crosses the living tissue 100 (100A). Therefore, the optical path length extending to the light-detecting surface 31 of the light-detecting element 3 can be prolonged, and hence the reduction of the accuracy of the acquisition of a biological signal and due to reduction of the SN ratio of the intensity signal can be suppressed. Mainly due to Condition 3, at least light which is on the optical axis 21 to have the highest intensity enters the light-detecting surface 31. Even in the case where the optical path length is prolonged according to Condition 2, or where the probe 1 is attached to the living tissue 100A that is relatively thick, therefore, the reduction of the accuracy of the acquisition of a biological signal and due to reduction of the absolute value of the signal intensity can be suppressed. As a result of the synergistic effect of the conditions, the biological signal can be accurately acquired irrespective of the thickness of the living tissue of the subject.

FIG. 2A schematically illustrates the configuration of a probe 1A of a second embodiment. Components which are identical or equivalent to those of the probe 1 of the first embodiment will be denoted by the same reference numerals, and duplicated explanations will be omitted.

In the probe 1A of this embodiment, the light-detecting element 3 is supported by the second supporting portion 52 so that the light-detecting surface 31 is inclined with respect to the direction orthogonal to the second attachment surface 51 of the second support 5 (the direction indicated by the arrow B in the figure).

FIG. 2B illustrates a case where the probe 1A is attached to the living tissue 100A which is thicker than the living tissue 100 shown in FIG. 2A. In both the cases, the three conditions described in connection with the probe 1 of the first embodiment are satisfied.

According to the configuration, the direct incidence of the light emitted from the light-emitting element 2, on the light-detecting surface 31 can be enhanced. As compared to the probe 1 of the first embodiment, therefore, it is possible to respond to a request for further enhancing the signal intensity in a range where the light-detecting element 3 is not saturated. Consequently, the biological signal can be accurately acquired irrespective of the thickness of the living tissue of the subject.

FIG. 3A illustrates a first modified example of the probe 1A of the second embodiment. In this example, the first passage 43 of the first support 4 is gradually expanded toward the first attachment surface 41, and the second passage 53 of the second support 5 is gradually expanded toward the second attachment surface 51.

According to such a configuration, the intensity of the light which is passed through the first passage 43 and the second passage 53 can be increased. As compared to the probe 1A of the second embodiment, therefore, it is possible to respond to the demand for further enhancing the signal intensity in the range where the light-detecting element 3 is not saturated. Consequently, the biological signal can be further accurately acquired irrespective of the thickness of the living tissue of the subject.

A configuration wherein only one of the first passage 43 and the second passage 53 is gradually expanded may be employed in accordance with a required signal intensity. The configuration of the modification may be applied to the probe 1 of the first embodiment.

FIG. 3B illustrates a second modified example of the probe 1A of the second embodiment. In this example, the first passage 43 of the first support 4 extends in the direction of the optical axis 21. The second passage 53 of the second support 5 extends toward the first passage 43 so as to obliquely cross the second attachment surface 51.

According to such a configuration, the light is scattered in the living tissue 100 (100A), and the intensity of the light which is passed through the second passage 53 can be reduced. Therefore, as compared to the probe 1A of the second embodiment, it is possible to respond to the demand for further enhancing the SN ratio in the range where the light-detecting element 3 is not saturated. Consequently, the biological signal can be further accurately acquired irrespective of the thickness of the living tissue of the subject.

One of the first passage 43 and the second passage 53 may not satisfy the above-described conditions in accordance with a required signal intensity. The configuration of the modification may be applied to the probe 1 of the first embodiment.

The above-described embodiments are mere examples for facilitating understanding of the invention. The configurations of the embodiments may be adequately changed or improved without departing the concept of the invention. It is obvious that equivalents are included within the technical scope of the invention.

In the above-described embodiments, the first passage 43 and the second passage 53 are described as hollow spaces. However, at least one of the first passage 43 and the second passage 53 may have a configuration where the passage is filled with a transparent resin or the like, as far as the light emitted from the light-emitting element 2 can be transmitted through the passage.

What is claimed is:

1. A probe comprising:
   a light emitter having an optical axis;
   a light detector having a light-detecting surface configured to detect light emitted from the light emitter, and configured to output a signal in accordance with intensity of the light;
   a first support having: a first attachment surface adapted to be attached to a first portion of a living tissue of a subject; a first supporting portion supporting the light emitter; and a first passage configured to allow the light emitted from the light emitter to pass through; and a second support having: a second attachment surface adapted to be attached to a second portion of the living tissue of the subject; a second supporting portion supporting the light detector; and a second passage configured to allow the light having passed through the second portion to pass through, wherein the light emitter is supported by the first supporting portion such that the optical axis is inclined relative to a direction orthogonal to the first attachment surface;

wherein the light detector is supported by the second supporting portion such that the optical axis is extended onto the light-detecting surface under a condition that the first attachment surface is attached to the first portion of the living tissue and the second attachment surface is attached to the second portion of the living tissue, wherein the second passage is located such that a centerline of the second passage does not cross a centerline of the first passage under the condition that the first attachment surface is attached to the first portion of the living tissue and the second attachment surface is attached to the second portion of the living tissue, and wherein an opening of the first passage at the first attachment surface is parallel to an opening of the second passage at the second attachment surface.

2. The probe of claim 1, wherein the light detector is supported by the second supporting portion such that the light-detecting surface is inclined relative to a direction orthogonal to the second attachment surface.

3. The probe of claim 1, wherein the first passage is expanding toward the first attachment surface.

4. The probe of claim 1, wherein the first passage is extending in a direction along the optical axis.

5. The probe of claim 1, wherein the second passage is expanding toward the second attachment surface.

6. The probe of claim 1, wherein the second passage is extending toward the first passage while crossing the second attachment surface obliquely.

7. The probe of claim 1, wherein the first attachment surface opposes the second attachment surface.

8. The probe of claim 1, wherein the first attachment surface and second attachment surface overlap along a direction orthogonal to the second attachment surface.

9. The probe of claim 1, wherein the centerline of the second passage extends along a direction orthogonal to the second attachment surface, and the centerline of the first passage extends along the direction orthogonal to the first attachment surface.

10. A probe comprising:
a light emitter having an optical axis;
a light detector having a light-detecting surface configured to detect light emitted from the light emitter, and configured to output a signal in accordance with intensity of the light;

a first support having: a first attachment surface adapted to be attached to a first portion of a living tissue of a subject; a first supporting portion supporting the light emitter; and a first passage configured to allow the light emitted from the light emitter to pass through; and a second support having: a second attachment surface adapted to be attached to a second portion of the living tissue of the subject; a second supporting portion supporting the light detector; and a second passage configured to allow the light having passed through the second portion to pass through, wherein the light emitter is supported by the first supporting portion such that the optical axis is inclined relative to a direction orthogonal to the first attachment surface, wherein the light detector is supported by the second supporting portion such that the optical axis is extended onto the light-detecting surface under a condition that the first attachment surface is attached to the first portion of the living tissue and the second attachment surface is attached to the second portion of the living tissue, wherein the second passage is located such that no portion of the second passage overlaps with the first passage as seen from a direction orthogonal to the second attachment surface under the condition that the first attachment surface is attached to the first portion of the living tissue and the second attachment surface is attached to the second portion of the living tissue, wherein a distance between the first attachment surface and the second attachment surface along the direction orthogonal to the second attachment surface is less than a distance between the light emitter and the light detector, and wherein an opening of the first passage at the first attachment surface is parallel to an opening of the second passage at the second attachment surface.

11. The probe of claim 10, wherein the light detector is supported by the second supporting portion such that the light-detecting surface is inclined relative to the direction orthogonal to the second attachment surface.

12. The probe of claim 10, wherein the first passage is expanding toward the first attachment surface.

13. The probe of claim 10, wherein the first passage is extending in a direction along the optical axis.

14. The probe of claim 10, wherein the second passage is expanding toward the second attachment surface.

15. The probe of claim 10, wherein the second passage is extending toward the first passage while crossing the second attachment surface obliquely.

16. The probe of claim 10, wherein the first attachment surface opposes the second attachment surface.

17. The probe of claim 10, wherein the first attachment surface and second attachment surface overlap along the direction orthogonal to the second attachment surface.

* * * * *